(12) United States Patent
Wolpo (10) Patent No.: US 9,636,195 B2
(45) Date of Patent: May 2, 2017

(54) HANDS FREE ORAL HYGIENE SYSTEM

(71) Applicant: Stephen H. Wolpo, Stamford, CT (US)

(72) Inventor: Stephen H. Wolpo, Stamford, CT (US)

( * ) Notice: Subject to any disclaimer, the term of this patent is extended or adjusted under 35 U.S.C. 154(b) by 0 days.

(21) Appl. No.: 14/038,186

(22) Filed: Sep. 26, 2013

(65) Prior Publication Data
US 2014/0093836 A1    Apr. 3, 2014

Related U.S. Application Data

(60) Provisional application No. 61/707,550, filed on Sep. 28, 2012.

(51) Int. Cl.
*A61C 3/00* (2006.01)
*A61C 17/22* (2006.01)
(Continued)

(52) U.S. Cl.
CPC ........ *A61C 17/228* (2013.01); *A46B 15/0024* (2013.01); *A61C 3/005* (2013.01);
(Continued)

(58) Field of Classification Search
CPC . A61C 17/228; A61C 17/0211; A61C 17/349; A61C 17/222; A61C 17/3481;
(Continued)

(56) References Cited

U.S. PATENT DOCUMENTS 3,215,139 A    11/1965 Dietz
3,401,690 A *  9/1968 Martin ............................ 604/22
(Continued)

FOREIGN PATENT DOCUMENTS

WO    2004108008 A1    12/2004
WO    2012088193 A2     6/2012

OTHER PUBLICATIONS

International Search Report and Written Opinion of the International Searching Authority Application No. PCT/US2013/062219 Completed: Feb. 10, 2014; Mailing Date: Feb. 24, 2014 10 pages.

*Primary Examiner* — Cris L Rodriguez
*Assistant Examiner* — Matthew Saunders
(74) *Attorney, Agent, or Firm* — St. Onge Steward Johnston & Reens, LLC (57) ABSTRACT

An oral hygiene system for cleaning teeth and gums includes a mouthpiece having at least one arcuate channel adapted to receive and surround the teeth. The mouthpiece includes at least two modalities chosen from a mechanical modality, an iontophoretic modality, and a disinfection modality. The mechanical modality brushes the teeth and gums and dislodges food debris, the iontophoretic modality breaks up plaque and tartar buildup, and the disinfection modality removes the food debris, plaque and tartar buildup. A control system coordinates the transmission of modalities, tracks and records utilization, recording completed and failed treatment cycles, and transmits them to a monitoring system. The monitoring system, which links to electronic medical administrating record (eMAR) technology and patient tracking technology (e.g., RFID sensors, electronic tags), facilitates compliance with recommended oral hygiene regimens and review of compliance by medical staff, assisted living staff, and/or caregivers.

19 Claims, 4 Drawing Sheets

(51) Int. Cl.
*A61N 1/32* (2006.01)
*A61C 17/02* (2006.01)
*A61C 17/34* (2006.01)
*A61N 1/05* (2006.01)
*A46B 15/00* (2006.01)
*A61C 19/06* (2006.01)
*A61C 17/20* (2006.01)

(52) U.S. Cl.
CPC ...... *A61C 17/0208* (2013.01); *A61C 17/0211* (2013.01); *A61C 17/222* (2013.01); *A61C 17/3481* (2013.01); *A61N 1/0548* (2013.01); *A61N 1/322* (2013.01); *A61N 1/325* (2013.01); *A61C 17/20* (2013.01); *A61C 19/063* (2013.01)

(58) Field of Classification Search
CPC ......... A61C 17/20; A61C 17/22; A61C 17/28; A61C 17/30; A61C 17/005; A61C 19/063; A46B 2200/1066; A46B 9/045; A46B 13/06; A46B 15/0022; A61K 2800/83; A61N 1/03; A61N 1/0548; A61N 1/322; A61N 1/325
USPC .................. 433/32, 80, 216; 15/21.1, 321
See application file for complete search history.

(56) References Cited

U.S. PATENT DOCUMENTS

| | | | |
|---|---|---|---|
| 3,440,680 A | | 4/1969 | Werding |
| 3,489,141 A | * | 1/1970 | Warren, Jr. ................. 601/164 |
| 3,520,297 A | | 7/1970 | Bechtold |
| 3,566,869 A | * | 3/1971 | Crowson ......................... 433/80 |
| 3,731,675 A | * | 5/1973 | Kelly ............................. 601/164 |
| 4,224,710 A | * | 9/1980 | Solow ............................ 15/22.1 |
| 4,237,574 A | | 12/1980 | Kelly et al. |
| 4,244,373 A | * | 1/1981 | Nachman ............... A61B 17/58 |
| | | | 607/50 |
| 5,337,435 A | * | 8/1994 | Krasner et al. .................... 15/23 |
| 5,365,624 A | * | 11/1994 | Berns ............................. 15/22.1 |
| 5,443,386 A | | 8/1995 | Viskup |
| 6,152,733 A | | 11/2000 | Hegemann et al. |
| 6,893,259 B1 | | 5/2005 | Reizenson |
| 7,044,737 B2 | | 5/2006 | Fu |
| 7,118,377 B2 | | 10/2006 | Inoue et al. |
| 7,537,451 B1 | | 5/2009 | Ramnarine |
| 8,241,035 B2 | * | 8/2012 | Jones et al. .................... 433/29 |
| 2003/0203336 A1 | | 10/2003 | Somodi |
| 2007/0009856 A1 | * | 1/2007 | Jones et al. .................. 433/215 |
| 2007/0184404 A1 | * | 8/2007 | Johnki ............................. 433/80 |
| 2008/0003540 A1 | * | 1/2008 | Khawaled et al. ........... 433/215 |
| 2008/0199830 A1 | * | 8/2008 | Fontenot .............. A46B 5/0012 |
| | | | 433/215 |
| 2009/0208898 A1 | | 8/2009 | Kaplan |
| 2009/0276972 A1 | | 11/2009 | Dugan |
| 2010/0324460 A1 | | 12/2010 | Van Der Rijt et al. |
| 2011/0072605 A1 | | 3/2011 | Steur |
| 2011/0154595 A1 | | 6/2011 | Hill |
| 2011/0247159 A1 | | 10/2011 | Steur et al. |
| 2011/0258792 A1 | | 10/2011 | Steur et al. |
| 2011/0318705 A1 | | 12/2011 | Sullivan et al. |
| 2012/0077144 A1 | * | 3/2012 | Fougere et al. ................. 433/82 |
| 2012/0141954 A1 | | 6/2012 | Headstrom et al. |
| 2012/0189976 A1 | * | 7/2012 | McDonough et al. ......... 433/89 |
| 2013/0236851 A1 | * | 9/2013 | McDonough et al. ......... 433/89 |
| 2013/0260332 A1 | * | 10/2013 | Shapiro .......................... 433/80 |
| 2015/0024340 A1 | * | 1/2015 | De Gentile .................... 433/82 |

* cited by examiner

HANDS FREE ORAL HYGIENE SYSTEM

FIELD OF THE INVENTION

This invention relates to a dental hygiene system and more specifically to a hands-free oral hygiene system that maintains or improves a user's oral health by breaking down and removing plaque from the teeth and gums, brushing the teeth and gums, and irrigating the teeth and gums with disinfecting fluid.

BACKGROUND OF THE INVENTION

It is well known that an effective method of maintaining oral hygiene is cleaning the teeth and gingival regions on a daily basis. The conventional method of cleaning teeth involves flossing the teeth as well as brushing the teeth and gums with dentifrice (e.g., toothpaste, tooth powder) using a toothbrush. In addition to brushing the teeth, the conventional method may include the step of rinsing the teeth and gums with antiseptic fluid or mouthwash to kill bacterial plaque which can cause white-spot lesions, dental caries (e.g., tooth decay and cavities), and gingivitis. However, the conventional method of oral care requires a significant number of steps involving coordinated movement of the hands and mouth. For example, a person must stand in front of a mirror, tear a piece of floss, insert the floss between the teeth gently sliding the floss up and down, curve the floss around the base of each tooth, making sure the floss goes beneath the gumline, thereafter grip a tooth brush, apply toothpaste to the bristles of the toothbrush, properly orient the toothbrush so that the bristles contact the surfaces of the teeth (e.g., buccal, labial, lingual, occlusal) as well as the gum line, perform a repetitive brushing motion for at least two minutes, and then expel toothpaste suds. Further, the person must measure an amount of mouthwash, pour it into the mouth, gargle for a period of time, and thereafter expel the spent mouthwash.

Because of the laborious steps involved in the conventional form of oral care, many people fail to properly clean their teeth. This is especially true for children, who often do not know or understand the importance of flossing, properly positioning the toothbrush bristles against the teeth, and performing the repetitive brushing motion for at least two minutes. Generally, people often do not brush their teeth for the suggested amount of time and do not rinse their mouth with an antiseptic fluid. Moreover, people suffering from physical and/or mental disabilities are unable to follow the conventional oral care method because they either have limited dexterous abilities or lack the mental capacity to perform the steps involved therein.

In order to promote effective oral care, dental devices have been developed which simplify the steps needed to properly clean teeth. For example, U.S. Pat. No. 4,237,574 to Kelly et al. discloses a mouthpiece with a plurality of brush heads disposed along an inner channel and ultrasonic means for vibrating the brush heads. Kelly further discloses a different mouthpiece, wherein, instead of using brush heads, a fluid medium is supplied to and discharged from the mouth piece, wherein the fluid medium is used to transmit ultrasonic energy to the teeth. These two devices, however, fail to clean between the teeth, where buildup of plaque and tartar is common. The bristles on the brush heads do not extend and reach between the teeth. Further, the mere use of a fluid medium to clean the teeth is not as effective as scrubbing them with brush heads. In other words, the energy transmitted by the fluid to the teeth during rinsing is not sufficient alone to break up plaque deposits on the teeth.

U.S. Pat. No. 7,118,377 to Inoue et al. and U.S. Pat. No. 6,893,259 to Reizenson and U.S. Patent Application No. 2011/0318705 to Sullivan et al. each describe a dental system adapted to clean a person's teeth and gingival regions using a disinfection modality. Each system comprises a mouthpiece, a supply tube connecting the mouthpiece to a supply unit, a drain tube connecting the mouthpiece to a drain unit, and a pump unit for introducing a cleaning solution into the mouthpiece through the supply tube and removing spent solution through the drain tube. However, the systems disclosed in these references fail to provide adequate means for removing plaque on the surfaces of teeth, in the gingival crevices between the teeth and gums, and in the teeth crevices. Moreover, it is generally agreed upon that the mere use of a cleaning solution, such as mouthwash, does not provide an effective means of cleaning teeth and does not eliminate the need for brushing and flossing.

While the prior art dental systems provide some benefits in oral maintenance, they still suffer from several disadvantages. One such disadvantage is that these dental systems fail to effectively clean the crevices between teeth where plaque and tartar commonly accumulate. Further, the prior art dental systems do not provide a comprehensive, synergistic treatment of the teeth and gums, which includes plaque-removing, cleaning, disinfecting, and preventative modalities.

SUMMARY OF THE INVENTION

Accordingly, it is an object of the present invention to provide a hands-free oral hygiene system which is adapted to clean teeth and promote oral care for people of all ages as well as people with physical and mental disabilities, including people who are handicapped or lack dexterity in performing tasks with their hands.

It is another object of the present invention to provide an oral hygiene system which cleans the surfaces of teeth (e.g., buccal, labial, lingual, occlusal), the gingival crevices, and the crevices between teeth.

It is a further object of the present invention to provide an oral hygiene system which removes plaque and tartar from the teeth as well as cleans, disinfects and applies protective elements to the teeth. It is also an object of the present invention to perform the above tasks in a coordinated manner—for example, simultaneously—in order to achieve a synergistic effect.

It is yet another object of the present invention to provide an oral hygiene system which removes plaque and tartar from the teeth as well as cleans, disinfects and applies protective elements to a plurality of teeth and more specifically to an entire row of teeth (i.e., maxillary/upper teeth, mandibular/lower teeth).

It is another objective of the present invention to provide an oral hygiene system which can monitor and track utilization and treatment sessions as well as track and collect patient care information.

These and other objectives are achieved by providing a hands-free oral hygiene system for cleaning teeth and gums, wherein the system includes a mouthpiece which has at least one arcuate channel adapted to receive and surround the teeth and which transmits at least two modalities chosen from a group consisting of a mechanical modality, an iontophoretic modality, and a disinfection modality. The mechanical modality brushes the teeth and gums and dislodges food debris. The iontophoretic modality breaks up plaque and tartar that has built up on the surfaces of the teeth, in the gingival crevices between the teeth and gum line, and in the crevices between adjacent teeth. The disinfection modality irrigates the teeth and gums in order to remove any food debris, plaque and tartar buildup. In addition, the disinfection modality is adapted to kill bacteria present on the teeth and gums and apply a protective layer on the teeth to prevent tooth decay and/or gingivitis.

Noted herein, the terms "transmit" and "transmission" are used interchangeably with the words "provide" and "provision" and thus signify the provision of a modality.

Other objectives of the invention are achieved by providing an oral hygiene system for maintaining oral care of teeth and gums, wherein the system includes a mouthpiece for receiving and surrounding the teeth and gums, the mouthpiece being adapted to include and transmit in a coordinated sequence at least two modalities chosen from a group consisting of a mechanical modality, an iontophoretic modality, and a disinfection modality. The transmission or provision of the at least two modalities provides a comprehensive, synergistic oral care treatment, thereby maintaining or improving the health of the teeth and gums. In some embodiments, the at least two modalities are transmitted simultaneously. In other embodiments, the coordinated sequence is defined by a sequential transmission of the at least two modalities by the mouthpiece.

The coordinated sequence may be defined by the length of time in which any one of the at least two modalities is used to treat the teeth and gums. In a preferred embodiment, the overall oral treatment provided by the oral hygiene system lasts for at least two minutes. However, in some embodiments, the time with which the oral hygiene system cleans the teeth and gums may be less than two minutes. The oral hygiene system is able to sufficiently clean the teeth and gums in less than two minutes due to the synergistic effect of transmitting the at least two modalities.

Additional objectives of the invention are achieved by providing an oral hygiene system having a mouthpiece with at least one arcuate channel for receiving and surrounding the teeth and gums and at least one structural rim, wherein the structural rim is adapted to make sealing contact with the gums. The at least one arcuate channel and the at least one structural rim, subsequently, form a sealed enclosure or chamber around the teeth. The sealed enclosure is adapted to direct and focus the transmission of at least two modalities chosen from the group consisting of a mechanical modality, an iontophoretic modality, and a disinfection modality. The beneficial effects provided by the at least two modalities, therefore, may be concentrated directly at the teeth, gingival crevices, and teeth crevices.

Further objectives are achieved by providing an oral hygiene system that includes a mouthpiece having at least one arcuate channel and an insert releasably coupled to the arcuate channel, wherein the mouthpiece transmits at least two modalities chosen from a group consisting of a mechanical modality, an iontophoretic modality, and a disinfection modality. The insert is configured to extend and cover the entire length/span of the arcuate channel. The insert comprises two opposing vertical walls mounted to a base wall, creating a substantially U-shaped configuration. Once coupled to the mouthpiece, the insert is adapted to transmit the mechanical modality and the disinfection modality. Further, the releasable attachment feature of the insert provides for quick and easy means of sanitizing the mouthpiece and the components therein. Alternatively, an insert that has been used and "soiled" can be easily detached from the mouthpiece and replaced with a new insert.

For the transmission of the mechanical modality, the insert includes a first set of brush heads attached to one of the vertical walls, a second set of brush heads attached to another of the vertical walls, and a third set of brush heads attached to the base wall, wherein the first, second, and third sets of brush heads project inwardly relative to the U-shaped configuration of the insert. Each brush head comprises a plurality of bristles that is adapted to contact and scrub the surfaces of the teeth (buccal, labial, lingual, occlusal) and gums. In some embodiments, the brush heads are configured to vibrate in multiple axes. In other embodiments, the brush heads are configured to oscillate in one axis. In yet other embodiments, the brush heads are configured to oscillate in a rotational manner. The mechanism for driving the brush heads can be established at a sonic frequency, and thus the brush heads can vibrate at a frequency of less than 20,000 hertz. Alternatively, the brush heads can be driven in an ultrasonic manner at a frequency of 20,000 hertz or higher.

For the transmission of the disinfection modality, the insert includes at least one inlet port disposed in each of the vertical walls, the inlet ports supplying aqueous-based fluid, and preferably disinfecting fluid, to the mouthpiece and thereby irrigating the teeth and gums. In some embodiments, the inlet ports are adapted to spray or release with force the disinfecting fluid. This helps to dislodge food debris and/or breakup plaque and tartar buildup. The insert also includes at least one outlet port disposed in the base wall proximate to one of the vertical walls, the outlet port being adapted to remove the disinfecting fluid, food debris, plaque and tartar buildup. In some embodiments, the insert includes at least two outlet ports, one outlet port being positioned at a corner formed between the base wall and one of the vertical walls and another outlet port being positioned at a corner formed between the base wall and the other vertical wall. The outlet ports may be adapted to provide a suction force in order to assist in removing the disinfecting fluid, food debris, plaque and tartar.

The iontophoretic modality comprises at least one electrode positioned in the mouthpiece, wherein the electrode is adapted to contact the gums and apply an electric charge to the teeth. The application of the electric charge depolarizes the adherence bonding of plaque and tartar, and thus loosens and breaks up any buildup of plaque and tartar. It is noted that the electric charge is minor and does not cause any pain to the teeth or gums.

In some embodiments, the mouthpiece includes at least two electrodes for the transmission of the iontophoretic modality. In particular, a first electrode is positioned in the mouthpiece outside the arcuate channel such that it contacts the gums. A second electrode is positioned inside the arcuate channel in a manner such that it does not touch the teeth and gums. The first electrode is adapted to apply an electric charge to the teeth, wherein the electric charge travels from the gums to the teeth as a result of an electric potential generated between the first and second electrodes.

Additional objectives are achieved by providing a hands-free oral hygiene system for cleaning teeth and gums, wherein the system includes a mouthpiece transmitting at least two modalities chosen from a group consisting of a mechanical modality, an iontophoretic modality, and a disinfection modality, as well as a control unit (controller) for controlling the mouthpiece and the transmission of the at least two modalities according to a coordinated sequence. Through the control unit, the system can provide an effective oral treatment wherein the mechanical modality brushes the teeth and gums and dislodges food debris, the iontophoretic modality breaks up plaque and tartar buildup, and the disinfection modality removes the food debris, plaque and tartar buildup.

The control unit comprises a control system which monitors and tracks utilization of the oral hygiene and patient care. The control system, in particular, can monitor the time of day and the treatment cycle/session activation. The control system records whether a treatment session was completed or failed to complete, and if failure occurs, it records the particular problem or source of the failure. The control system transmits the above data, through wired or wireless communication technology, to a monitoring system. The control system and monitoring system may be linked to eMAR (electronic Medication Administration Record) utilizing technology, present in hospitals and long term care facilities, to automatically document the administration of medication into certified EHR (electronic health record) technology, using electronic tracking sensors (for example, radio frequency identification (RFID) or electronically readable tagging such as bar coding). As a result, the monitoring system facilitates better compliance with recommended oral hygiene regimens.

The oral hygiene system may further be adapted with a pump unit for transmitting the disinfection modality, such that the pump unit supplies fluid, and preferably disinfecting fluid, to the mouthpiece and removes spent fluid (i.e., disinfecting fluid with food debris, plaque and tartar) from the mouthpiece.

Further objectives are achieved by providing a hands-free oral hygiene system that includes a mouthpiece, wherein the mouthpiece has at least one arcuate channel adapted to receive and surround the teeth and gums, and transmits a mechanical modality, an iontophoretic modality, and a disinfection modality in a coordinated sequence.

Other objects of the invention and its particular features and advantages will become more apparent from consideration of the following drawings and accompanying detailed description. It should be understood that the detailed description and specific examples, while indicating the preferred embodiment of the invention, are intended for purposes of illustration only and are not intended to limit the scope of the invention.

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

Figure 1:
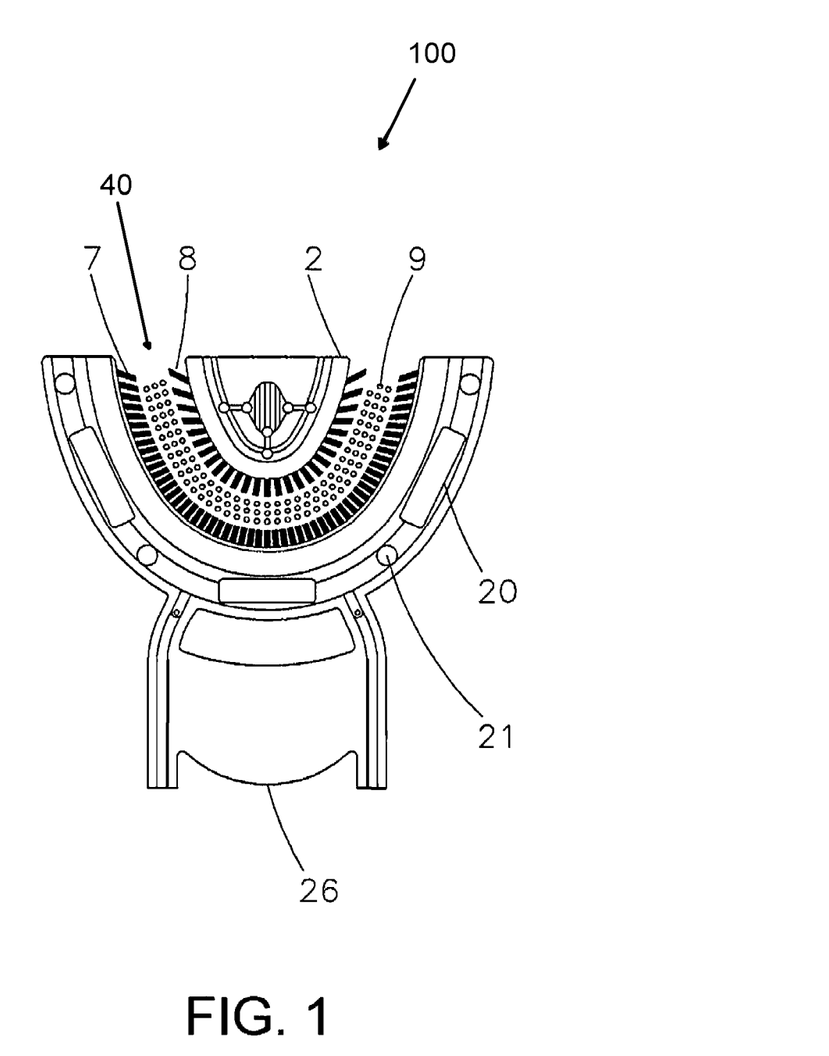
FIG. 1 is a top view of the hands-free oral hygiene system according to an exemplary embodiment of the present invention.
Figure 2:
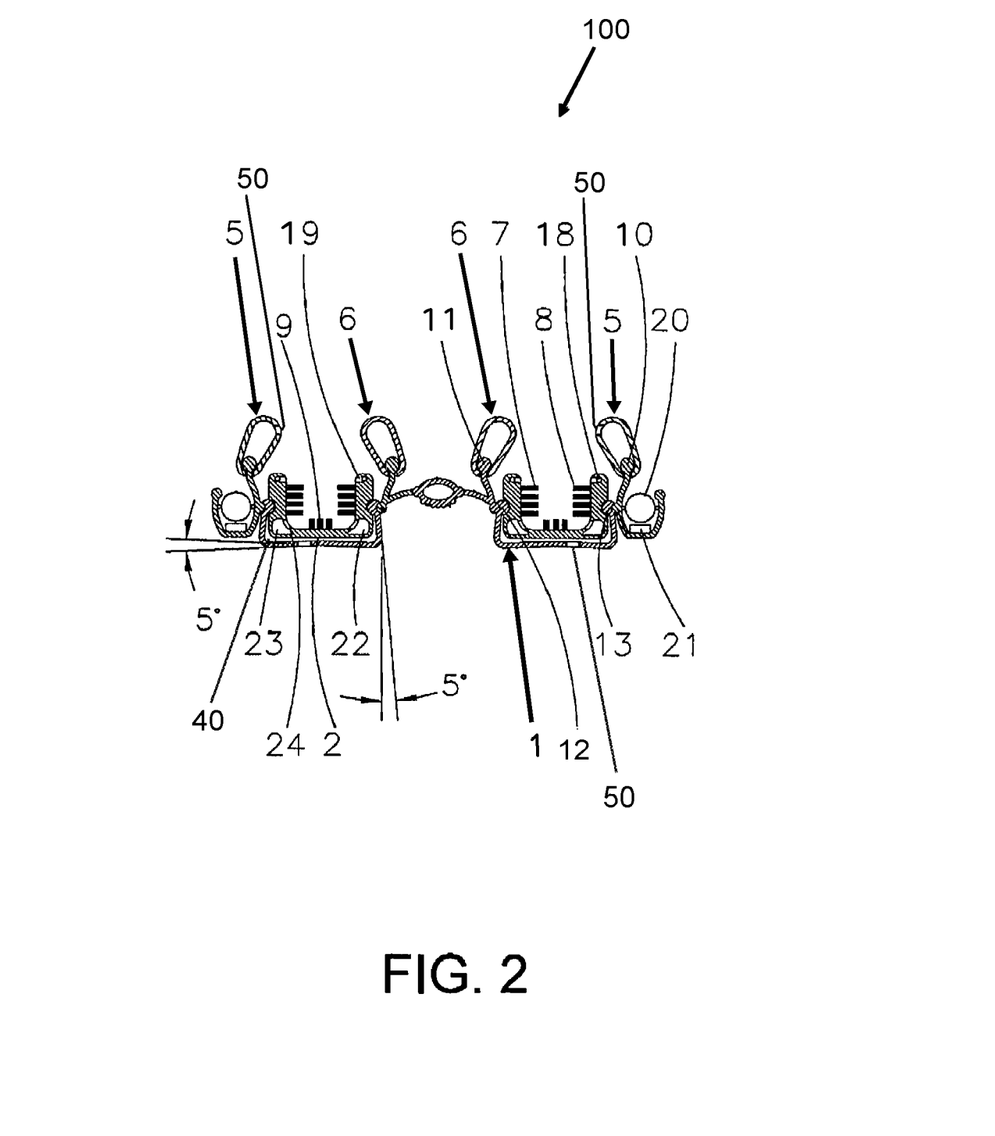
FIG. 2 is a sectional view of the hands-free oral hygiene system of FIG. 1.

Referring to the figures in detail and first to FIGS. 1-2, there is shown an exemplary embodiment of a hands-free oral hygiene system for cleaning teeth and gums. FIGS. 1-2 illustrate oral hygiene system 100 formed within the structure of a mouthpiece frame 1. The mouthpiece 1 is elastic and can conform to the shape of a user's oral cavity (i.e., mouth). The mouthpiece 1 may be created using any material that is safe for intraoral contact and has elastic characteristics. For example, the mouthpiece 1 can be made of rubber, polyurethane, or another polymer. The mouthpiece 1 can be designed in any size to accommodate adults and children. In some embodiments, the mouthpiece 1 is customized to a particular user's oral cavity. In other embodiments, the mouthpiece 1 is available is several standard sizes (e.g., XS, S, M, L, XL.)

The mouthpiece 1 includes an arcuate channel 40 that is dimensioned for receiving and surrounding the teeth and gums. As shown in FIG. 2, the arcuate channel 40 of the mouthpiece 1 has a substantially U-shaped cross-section profile.

The mouthpiece 1 further includes two structural rims, an inner rim 6, 11 and an outer rim 5, 10, which extend substantially vertical from the sides of the arcuate channel of the mouthpiece 1. The inner rim 6, 11 is adapted to form a seal with the gums adjacent to the lingual surfaces of the teeth (palatal mucosal seal) while the outer rim 5, 10 is adapted to form a seal with the gums adjacent to the buccal and labial surfaces of the teeth (labial mucosal seal). The combination of the arcuate channel, inner rim, and outer rim form a sealed enclosure or chamber around the teeth and gums such that fluids may not be communicated into or out of the mouthpiece and in particular, the arcuate channel 40. The mouthpiece 1 further includes retro molar pad seals 27 disposed at the ends of the arcuate channel. The pad seals 27 are adapted to contact, conform, and form a seal with the retro molars of the user's mouth, along the maxillae (upper jaw) or mandible (lower jaw). The inner rim 6, 11, outer rim 5, 10 and pad seals 27 are elastic such that they create a spring effect and naturally conform to the user's oral cavity (e.g., gums and retro molars).

The sealed enclosure created by the mouthpiece 1 around the teeth and gums provides a chambering effect which focuses and concentrates the oral care treatment provided by a mechanical modality, disinfection modality and/or an iontophoretic modality (discussed in further detail below). For example, the sealed enclosure provides for effective irrigation of the teeth and gums, by targeting fluid (e.g., disinfecting fluid) towards the teeth and gums, involved in the disinfection modality.

The system 100 further includes an insert 2 (FIGS. 2-3) that releasably couples to the arcuate channel 40 of the mouthpiece 1. The insert 2 is formed by a base wall 30 and two vertical walls 28, 29 (inner wall 29 and outer wall 28) mounted to and extending from opposing sides of the base wall 30. Accordingly, the insert 2 has a substantially U-shaped cross-section configuration. The insert may be made of any material that is safe for intraoral contact. However, unlike the mouthpiece 1, the insert 2 has a rigid structure.

To releasably attach the insert 2 within the arcuate channel, the mouthpiece 1 has at least one fastener disposed at or proximate to the arcuate channel. As shown in FIG. 2, the mouthpiece 1 comprises two fasteners 12, 13 to secure the insert 2 within the arcuate channel. In some embodiments, the fasteners 12, 13 may comprise snap fasteners, wherein the sides of the arcuate channel interlock with the vertical walls of the insert 2. The releasable attachment of the insert 2 with the mouthpiece 1 may be achieved by means of protrusions and recesses designed to fit each other. In one example, the fasteners are formed as one or more protrusions having a circular contour that correspond in shape to one or more recesses formed on the exterior side of the vertical walls of the insert. Once the protrusions are inserted into the recesses, the insert 2 and mouthpiece 1 are firmly connected, thereby inhibiting any movement between the two components.

For the mouthpiece 1 to transmit/provide a mechanical modality, the insert 2 is configured with a plurality of brush heads 7, 8, 9, wherein the brush heads are disposed along the entire length/span of the insert 2. More specifically, the brush heads 7 (lingual brush heads) are mounted on the inner vertical wall 29 of the insert 2 and are adapted to brush the lingual surfaces of the teeth and gums. The brush heads 8 (buccal and labial brush heads) are mounted on the outer vertical wall 28 of the insert 2 and are adapted to brush the buccal and labial surfaces of the teeth and gums. The brush heads 9 (occlusal brush heads) are mounted on the base wall 30 of the insert 2 and are adapted to brush the occlusal surfaces of the teeth. Further, the brush heads 7, 8, 9 are mounted such that they project inwardly with respect to the U-shaped configuration of the insert 2. Each of the brush heads included on the insert 2 comprises a plurality of bristles adapted to contact and brush the surfaces of the teeth and gums.

In some embodiments, the occlusal brush heads 9 are mounted perpendicularly with respect to the base wall 30 of the insert 2. The lingual brush heads 7 and the buccal and labial brush heads 8 may also be mounted perpendicularly relative to the vertical walls 28, 29 of the insert 2. However, in some embodiments, the lingual brush heads 7 and the buccal and labial brush heads 8 may be mounted obliquely or off-perpendicular with the vertical walls 28, 29. For example, the brush heads 7, 8 may be disposed at an angle such that they are partially pointed towards the gum line (e.g., the brush heads are angled away from the base wall of the insert). It is noted that when the bristles of the brush heads become worn, the insert 2 can be detached from the mouthpiece 1 and replaced with a new insert 2 having fresh (un-worn) brush heads. This feature allows for easy cleaning and maintenance of the oral hygiene system.

The mechanical modality further comprises at least one vibration device or actuator 20 disposed in the mouthpiece 1, wherein the actuator 20 is adapted to vibrate the brush heads 7, 8, 9 at sonic (e.g., less than 20,000 hertz) and/or ultrasonic frequencies (more than 20,000 hertz). The actuator 20, for example, may be a piezoelectric actuator, a micro-actuator, or nano-actuator. In some embodiments, the brush heads are adapted to vibrate in multiple axes. In other embodiments, the brush heads are configured to oscillate in one axis. In yet other embodiments, the brush heads are configured to oscillate in a rotational manner. By vibrating and/or oscillating the brush heads against the surfaces of the teeth and gums, the mechanical modality is able to scrub and clean the teeth as well as dislodge any food debris that may have accumulated between the teeth or within the gingival crevices.

The one or more actuators 20 are configurable such that bristle action can be driven at different frequencies between one treatment session (teeth cleaning) and a subsequent treatment session. The actuators can also vary (i.e., increasing and/or decreasing) the driving frequency within a single treatment session. For example, the actuators will initially vibrate the brush heads at a first frequency within the sonic region and then gradually increase the magnitude to a second frequency within the ultrasonic region. If the mouthpiece 1 has multiple actuators 20, the actuators can drive their respective brush heads at the same frequency or at different frequencies in a single treatment session. This characteristic of varying the driving frequency of the actuators helps to provide beneficial oral care customized to a particular user's oral health.

As shown in FIG. 1, the mouthpiece 1 has three actuators 20, wherein each actuator drives bristle action—using sonic or ultrasonic waves—for one of the brush head sets. However, the mouthpiece in some embodiments may be designed with one or two actuators. Where there is only one actuator, the brush heads 7, 8, 9 are collectively driven at the same frequency. In the embodiments where two actuators are included in the mouthpiece, different combinations of the brush heads 7, 8, 9 may be driven by the two actuators. One arrangement may comprise a first actuator driving the lingual brush heads 7 and the buccal and labial brush heads 8 and a second actuator driving the occlusal brush heads 9. Other arrangements of the two actuators and three sets of brush heads are possible. In further embodiments, the mouthpiece may have more than three actuators, which allows for subsets of the brush heads 7, 8 and/or 9 to be driven at different frequencies. For example, where four actuators are provided, two of the actuators may be assigned to the lingual brush heads 7, such that one actuator drives a subset of brush heads 7 aligned with the user's incisors and canine teeth while another actuator drives a subset of brush heads 7 aligned with the user's premolar and molar teeth. This feature is beneficial for user's who have sensitive teeth, as the actuators can be configured to provide low frequency vibrations to the brush heads that are aligned with the specific sensitive teeth. Alternatively, if certain teeth require extensive cleaning, the actuators can be configured to provide high frequency (e.g., ultrasonic) vibrations to the brush heads that are aligned with those teeth.

With regard to the disinfection modality, an aqueous-based disinfecting fluid, such as an antiseptic mouthwash, is provided via the insert 2 within the sealed enclosure of mouthpiece 1 to irrigate the teeth and gums and remove any food debris, plaque and tartar buildup. Further, the disinfecting fluid is adapted to kill bacteria present on the teeth and gums and/or apply a chemical layer (e.g., fluoride) to protect against tooth decay and gingivitis. The insert 2 has at least one inlet port 19 disposed in each of the vertical walls and at least one outlet port 24 disposed in the base wall proximate to one of the vertical walls (e.g., corner of insert 2 having a U-shaped configuration). The inlet ports 19 supplies disinfecting fluid to the teeth and gums while the outlet port 24 is adapted to discharge and remove the "spent" disinfecting fluid as well as food debris and plaque and tartar buildup. In the embodiment shown in FIG. 2, the insert 2 includes two inlet ports 19 and two outlet ports 24. One inlet port and one outlet port have openings that are directed substantially towards the lingual surfaces of the teeth. The other inlet port and outlet port have openings that are directed substantially towards the buccal/labial surfaces of the teeth. It is noted that reference to one inlet port or one outlet port may encompass a set of inlet ports or a set of outlet ports distributed along the span of the insert 2. Accordingly, there may be multiple locations along the insert 2 where disinfecting fluid is supplied into the sealed enclosure of the mouthpiece 1 and multiple locations along the insert 2 where spent fluid, food debris, plaque and tartar are removed.

Figure 3:
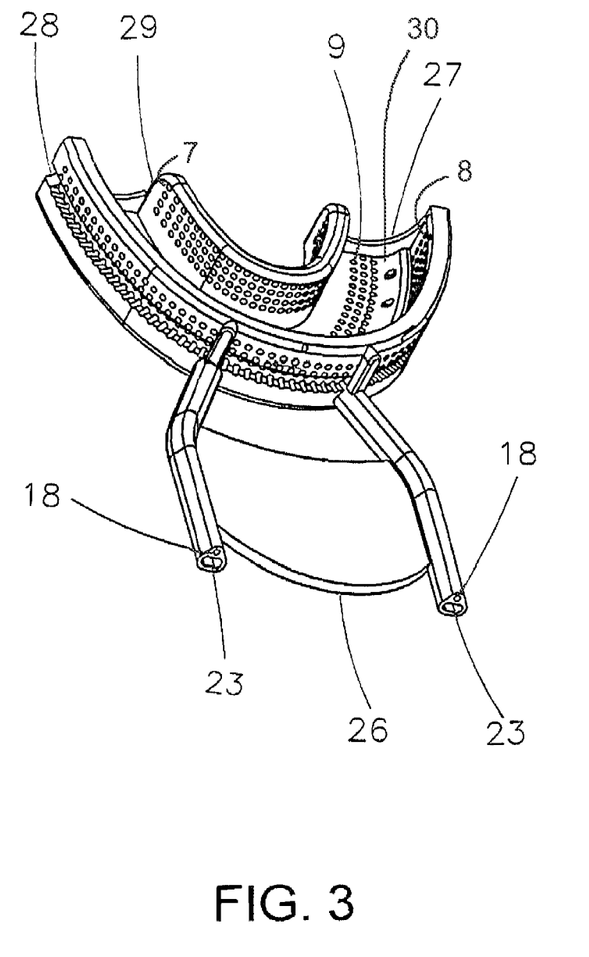
FIG. 3 is a perspective view of the hands-free oral hygiene system of FIG. 1.

The insert 2 also comprises at least one supply channel 18 in fluid communication with the inlet ports 19 and at least one discharge channel 22, 23 in fluid communication with the outlet ports 24. The supply channel 18 is adapted to feed the disinfecting fluid to the inlet ports 19 from a supply unit, which stores the disinfecting fluid. The discharge channel 22, 23 is adapted to discharge and remove spent fluid, food debris, plaque and tartar from the outlet ports to a drain unit, such as a sink or fluid collection device. As shown in FIGS. 2-3, the insert 2 has two supply channels 18 and two discharge channels 23 for circulating disinfecting fluid through the mouthpiece 1.

In some embodiments, the inlet ports 19 are adapted to spray, eject and release with force the disinfecting fluid. This feature of the inlet ports helps to thoroughly irrigate the teeth and gums as well as dislodge any food debris, plaque or tartar buildup. In some embodiments, the outlet ports 24 are adapted to provide a suction force in order to assist in removing the spent disinfecting fluid, food debris, plaque and tartar buildup. The suction force provided ensures that fluid, debris, plaque and tartar is removed continuously and reduces the likelihood that outlet ports 24 and discharge channels 22, 23 will be obstructed with debris, plaque and tartar.

In some embodiments, the oral hygiene system 100 includes a pump unit for communicating the disinfecting fluid from a supply unit, to and through the mouthpiece 1, and to a drain unit. In particular, the pump unit provides the ejection and suction capabilities of the inlet and outlet ports, respectively.

Figure 4:
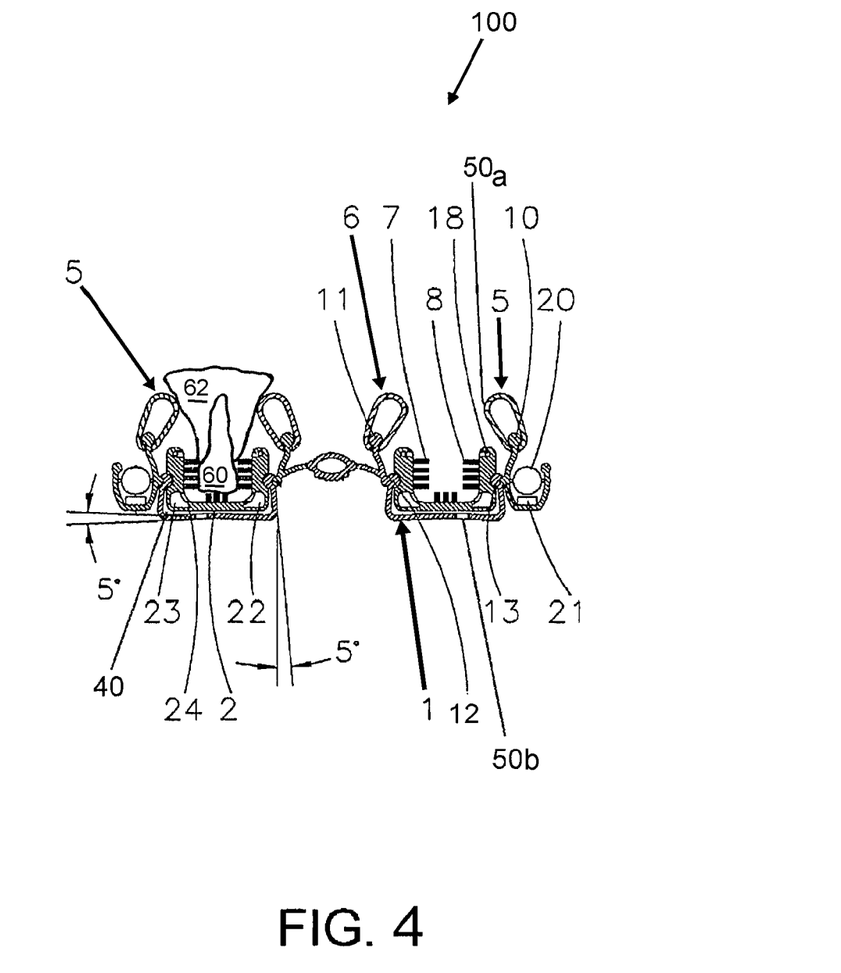
FIG. 4 is a sectional view of the hands-free oral hygiene system of FIG. 1 with teeth and gums positioned therein.

The iontophoretic modality comprises at least one electrode 50 positioned in the mouthpiece, wherein the electrode is adapted to contact the gums 62 (FIG. 4). In some embodiments, the electrode 50 may be positioned along one of the structural rims (inner rim 6, 11; outer rim 5, 10). With the electrode 50 being in contact with the gums 62, the electrode is adapted to apply an electrical charge to the teeth 60. The application of an electrical charge depolarizes the adherence bonding of plaque and tartar on the teeth, and thus loosens and breaks up any buildup of plaque and tartar. It is noted that the electric charge is minor and does not cause any pain to the teeth or gums of the user.

In some embodiments, the mouthpiece 1 includes at least two electrodes 50 for the transmission of the iontophoretic modality. In particular, as shown in FIG. 4, a first electrode 50a is positioned in the mouthpiece outside the arcuate channel such that it contacts the gums 62, i.e., disposed on one of the structural rims (e.g., outer rim 5, 10). Conversely, a second electrode 50b is positioned inside the arcuate channel in a manner such that it does not touch the teeth 60 and gums 62. For example, the second electrode 50b may be disposed within the arcuate channel of the mouthpiece 1 substantially adjacent to and under the base wall of the insert 2. The first electrode is adapted to apply an electric charge to the teeth, wherein the electric charge travels from the gums to the teeth as a result of an electric potential generated between the first and second electrodes.

With the iontophoretic modality loosening and breaking up the plaque and tartar that has accumulated on the teeth and gums, a comprehensive and synergistic oral care treatment is provided when combined with the mechanical and/or disinfection modalities.

In order to provide energy for the at least one actuator 20 to vibrate the brush heads and for the at least one electrodes to provide an electric charge, the oral hygiene system includes at least one power source 21 disposed in the mouthpiece 1. In some embodiments, the power source 21 comprises a 3V battery. In other embodiments, the power source 21 comprises a lithium cell. Regardless of the type of battery used, the power source 21 maintains a small profile and does not increase the size the mouthpiece 1 substantially. In some embodiments, power is supplied to the actuators and electrodes from an external power source, such as an electrical outlet, via an electric cable connected to the mouthpiece. Additionally, the external power source may be used to recharge the power source 21.

As shown in FIG. 1, the mouthpiece 1 generally has a parabolic profile resembling a row of teeth. The oral hygiene system 100 includes an armature platform 26, which extends out from the curved or convex side of the mouthpiece 1. More specifically, the armature platform 26 is positioned at and proximate to the vertex of the curved side of the mouthpiece. The platform 26 serves as a handle for a person (e.g., caregiver) to easily insert the mouthpiece 1 into an oral cavity or mouth. In some embodiments, the armature platform 26 provides support for the supply channels and discharge channels that are connected to a supply unit and drain unit, respectively.

In some embodiments of the hands-free oral hygiene system, the system includes the mouthpiece 1 for transmitting at least two modalities chosen from the group consisting of the mechanical modality, the iontophoretic modality, and the disinfection modality, and a control unit for controlling the mouthpiece 1 and the transmission of the at least two modalities according to a coordinated sequence. Via the control unit, a user is able to adjust and program which modalities to transmit, the sequence of transmission, and the length of time for transmitting a modality. In some embodiments, the control unit can be programmed so that the modalities are transmitted simultaneously. In other embodiments, the modalities may be transmitted sequentially. In still other embodiments, the modalities may be transmitted by a combination of simultaneous and sequential coordination. The control unit also provides means for configuring the actuators with respect to drive frequencies. Through the control unit, the user is able to establish whether the actuators maintain a constant drive frequency or vary drive frequency in a single treatment session.

The control unit is also adapted to record and track utilization of the oral hygiene system. For example, the control unit tracks when and how many times the system is turned on and off. It keeps track of whether the system is initialized and/or configured prior to a treatment session being provided to a person. In some embodiments, the control system is linked to sensors (e.g., pressure, temperature) positioned on the mouthpiece 1 to detect when the mouthpiece has been inserted into a person's mouth and the person is biting down on the mouthpiece. Information concerning the status of each component of the oral hygiene system is further collected by the control system in order to determine whether maintenance (e.g., equipment sterilization, equipment replacement, fluid refill) is required. For example, the control system may detect when a particular insert 2 needs to be replaced because the brush heads are worn and no longer provide effective brushing of the teeth. As another example, the control unit can monitor the fluid levels of a drain unit (e.g., fluid collection device) that is connected to the mouthpiece, thereby providing an indication or warning when the drain unit is almost full and needs to be emptied. In similar respect, the control unit can monitor the fluid levels of a supply unit (for providing disinfecting fluid) that is connected to the mouthpiece. The control system can also monitor pressure levels to determine whether fluid communication into, through, and out of the mouthpiece is laminar as well as detect if there are any obstructions at or near the inlet ports 19 and outlet ports 24 of the insert 2. If the control system recognizes that the ports are blocked, a warning signal or indication is provided. Additionally, the control system provides feedback on the status of connections between various components of the oral hygiene system. The control system detects whether the insert 2 has been properly positioned within the arcuate channel 40 of the mouthpiece 1. If the insert 2 and the mouthpiece 1 are misaligned, the control system provides an indication that the two components need to be repositioned to achieve alignment. The control system checks whether the connections between the at least one supply channel 18 and a supply unit (for supplying disinfecting fluid), between the discharge channels 22, 23 and a drain unit, and between a pump unit, the channels, the supply unit, and the drain unit are secure; if any loose connections are detected the control system will provide an appropriate warning signal and, in some cases, prevent the oral hygiene system from being engaged and providing treatment until after the issues/problems have been resolved.

In some embodiments, the control unit or system detects and registers whether a treatment cycle/session completed successfully or failed due to a problem. If the treatment session was interrupted or prematurely terminated for technical issues, the control unit gathers information regarding the particular component(s) of the oral hygiene system that are involved in the technical issue and provides assistance in diagnosing and resolving the issue. The control unit also gathers information pertaining to when (during what portion the treatment session) the technical issue occurred and how much of the treatment session was performed before termination. For example, if the disinfecting fluid supply unit or reservoir goes empty during a treatment session, the control unit will signal that the session failed and communicate which modality(ies) was being transmitted when the error occurred. The information concerning utilization and completed/failed treatment cycles is then transmitted—wirelessly or through wired communication lines—to a monitoring system. Through the monitoring system, a person (e.g., medical staff, assisted living staff, caregiver) can monitor and evaluate a patient's treatment and overall oral health, including when (e.g., time of day) a treatment session is activated. The control system and monitoring system may be linked to eMAR (electronic Medication Administration Record) utilizing technology, present in hospitals and long term care facilities, to automatically document the administration of medication into certified EHR (electronic health record) technology, using electronic tracking sensors (for example, radio frequency identification (RFID) or electronically readable tagging such as bar coding). As a result, the monitoring system in combination with eMAR facilitates better compliance with recommended oral hygiene regimens. Further, through the monitoring system, medical staff (i.e., dentist), assisted living staff, or caregivers can review a patient's oral care treatment with particular emphasis with compliance to oral hygiene regimens.

In yet other embodiments of the hands-free oral hygiene system, the mouthpiece 1 transmits all three modalities—mechanical modality, the iontophoretic modality, and the disinfection modality—in a coordinated sequence (e.g., simultaneous, sequentially, or combination thereof).

One skilled in the art will understand, in view of the foregoing description, that the hands-free oral hygiene system may be implemented with two of the mouthpieces so that oral care is provided to both the upper teeth and the lower teeth at the same time. In particular, one mouthpiece may be attached to, or placed adjacent to, another mouthpiece in a back-to-back configuration. Each such mouthpiece is adapted to transmit at least two modalities chosen from the group consisting of the mechanical modality, the iontophoretic modality, and the disinfection modality. Both mouthpieces may be configured to provide the same type of cleaning treatment to both upper and lower teeth, or alternatively, each mouthpiece may be independently configured to provide different types of cleaning treatment for the upper and lower teeth.

Although the invention has been described with reference to particular arrangement of parts, features, and the like, these are not intended exhaust all possible arrangements or features, and indeed many modifications and variations will be ascertainable to those of skill in the art.

What is claimed is:

1. An oral hygiene system for cleaning teeth and gums, the system comprising:
   a mouthpiece having at least one arcuate channel defined by an exterior sidewall and an interior sidewall, the arcuate channel adapted to receive and substantially surround a dental arch including an entire row of maxillary or mandibular teeth and gums in a mouth, said mouthpiece comprising at least one structural rim extending along the arcuate channel above at least one of the exterior sidewall and the interior sidewall; and
   an arcuate insert releasably coupled within said arcuate channel of said mouthpiece, said insert having a U-shaped cross section formed by two vertical walls and a base wall;
   a mechanical modality, comprised within said insert, that brushes the teeth and gums through direct contact and dislodges food debris;
   an iontophoretic modality that breaks up plaque buildup comprising a plurality of electrodes disposed in said mouthpiece, a first electrode being positioned in the at least one structural rim of said mouthpiece such that it contacts said gums and a second electrode being positioned in said arcuate channel and adjacent to said base wall of said insert such that it is out of contact with said teeth and gums;
   said first electrode generating an electric charge, said electric charge traveling from said gums to said teeth due to an electric potential generated between said first and second electrodes; and
   a disinfection modality that removes said food debris and plaque buildup.

2. The system of claim 1, wherein the mechanical modality, iontophoretic modality, and disinfection modality are transmitted simultaneously.

3. The system of claim 1, wherein the mouthpiece comprises at least one pad seal disposed at each end of the arcuate channel, said structural rim and pad seals adapted to make sealing contact with said gums; and
   wherein said at least one arcuate channel, said at least one structural rim, and said at least one pad seal disposed at each end of the arcuate channel form a sealed enclosure around said dental arch having said row of teeth and gums.

4. The system of claim 1, wherein the insert is adapted to comprise said disinfection modality.

5. The system of claim 1, wherein the mechanical modality comprises a first set of brush heads attached to a first vertical wall, a second set of brush heads attached to a second vertical wall, and a third set of brush heads attached to said base wall;
   said first, second, and third sets of brush heads projecting inwardly relative to said U-shaped configuration of said insert;

said brush heads each comprising a plurality of bristles adapted to contact surfaces of said teeth and gums.

6. The system of claim 5, wherein said third set of brush heads is disposed perpendicularly to said base wall.

7. The system of claim 5, wherein said first and second sets of brush heads are disposed perpendicularly to said first and second vertical walls, respectively.

8. The system of claim 5, wherein said first and second sets of brush heads are disposed obliquely to said first and second vertical walls, respectively.

9. The system of claim 5, wherein said mechanical modality comprises at least one actuator disposed in said mouthpiece, said actuator vibrating said brush heads in at least one axis.

10. The system of claim 4, wherein said disinfection modality comprises:
at least one inlet port disposed in at least one of said vertical walls of said insert, said inlet ports supplying disinfecting fluid to said teeth and gums; and
at least one outlet port disposed in said base wall proximate to one of said vertical walls, said outlet port removing said disinfecting fluid;
wherein said disinfecting fluid irrigates the teeth and gums, kills bacteria present thereon, and discharges said food debris and plaque buildup.

11. The system of claim 10, wherein said insert comprises:
at least one supply channel connected to said at least one inlet port, said supply channel providing fluid communication with a supply unit storing said disinfecting fluid; and
at least one discharge channel connected to said at least one outlet port, said discharge channel providing fluid communication with a drain unit for receiving said disinfecting fluid, food debris and plaque buildup.

12. The system of claim 1, wherein said electric charge depolarizes adherence bonding of said plaque buildup.

13. The system of claim 1 further comprising at least one power source, said power source supplying energy to the mouthpiece for the transmission of said mechanical modality and iontophoretic modality.

14. The system of claim 13, wherein said at least one power source is disposed in said mouthpiece.

15. An oral hygiene system for cleaning teeth and gums, the system comprising:
a mouthpiece having at least one arcuate channel defined by an exterior sidewall and an interior sidewall, the arcuate channel adapted to receive and substantially surround a dental arch including an entire row of maxillary or mandibular teeth and gums in a mouth, said mouthpiece comprising at least one structural rim extending along the arcuate channel above at least one of the exterior sidewall and the interior sidewall;
an arcuate insert releasably coupled within said arcuate channel of said mouthpiece, said insert having a U-shaped cross section formed by two vertical walls and a base wall;
a mechanical modality, comprised within said insert, that brushes the teeth and gums through direct contact and dislodges food debris;
an iontophoretic modality that breaks up plaque buildup comprising a plurality of electrodes disposed in said mouthpiece, a first electrode being positioned in the at least one structural rim of said mouthpiece such that it contacts said gums and a second electrode being positioned in said arcuate channel and adjacent to said base wall of said insert such that it is out of contact with said teeth and gums;
said first electrode generating an electric charge, said electric charge traveling from said gums to said teeth due to an electric potential generated between said first and second electrodes;
a disinfection modality that removes said food debris and plaque buildup; and
a control unit for controlling the mouthpiece and the transmission of the mechanical modality, the iontophoretic modality, and the disinfection modality according to a coordinated sequence.

16. An oral hygiene system for cleaning teeth and gums, the system comprising:
a mouthpiece having at least one arcuate channel defined by an exterior sidewall and an interior sidewall, the arcuate channel adapted to receive and substantially surround a dental arch including an entire row of maxillary or mandibular teeth and gums in a mouth, said mouthpiece is configured to be held in the mouth by interacting with oral anatomy and maintain position around the dental arch without intervention during operation of the oral hygiene system, wherein said mouthpiece comprises at least one structural rim extending along the arcuate channel above at least one of the exterior sidewall and the interior sidewall;
an arcuate insert releasably coupled within said arcuate channel of said mouthpiece, said insert having a U-shaped cross section formed by two vertical walls and a base wall;
a mechanical modality, comprised within said insert, that brushes the teeth and gums through direct contact and dislodges food debris;
an iontophoretic modality that breaks up plaque buildup comprising a plurality of electrodes disposed in said mouthpiece, a first electrode being positioned in the at least one structural rim of said mouthpiece such that it contacts said gums and a second electrode being positioned in said arcuate channel and adjacent to said base wall of said insert such that it is out of contact with said teeth and gums;
said first electrode generating an electric charge, said electric charge traveling from said gums to said teeth due to an electric potential generated between said first and second electrodes;
a disinfection modality that removes said food debris and plaque buildup;
a control unit for controlling the mouthpiece and the transmission of the mechanical modality, the iontophoretic modality, and the disinfection modality according to a coordinated sequence; and
a pump unit for actuating said disinfection modality, said pump unit supplying disinfecting fluid to the mouthpiece and removing spent fluid from the mouthpiece, said spent fluid comprising said disinfecting fluid, food debris and plaque buildup.

17. The oral hygiene system according to claim 1, wherein the insert is coupled between the exterior sidewall and the interior sidewall of said mouthpiece by fasteners is on each of the interior and exterior sidewalls of the arcuate channel interlocking with the vertical walls of the insert.

18. The oral hygiene system according to claim 15, wherein the insert is coupled between the exterior sidewall and the interior sidewall of said mouthpiece by fasteners on each of the interior and exterior sidewalls of the arcuate channel interlocking with the vertical walls of the insert.

19. The oral hygiene system according to claim 16, wherein the insert is coupled between the exterior sidewall and the interior sidewall of said mouthpiece by fasteners on each of the interior and exterior sidewalls of the arcuate channel interlocking with the vertical walls of the insert.

* * * * *